United States Patent [19]

Bates

[11] Patent Number: 4,817,836
[45] Date of Patent: Apr. 4, 1989

[54] RECEIVING BLANKET WITH SIDE SLEEVES

[76] Inventor: Joe B. Bates, Rte. 3, Box 295, Flint, Tex. 76115

[21] Appl. No.: 210,320

[22] Filed: Jun. 23, 1988

Related U.S. Application Data

[63] Continuation of Ser. No. 97,177, Sep. 11, 1987, abandoned.

[51] Int. Cl.[4] .............................................. A61G 1/00
[52] U.S. Cl. .................................... 224/158; 5/98 B; 604/356
[58] Field of Search ............................ 604/356, 357; 128/132 D; D6/603, 596; 224/158, 159, 223, 923; 5/98 B, 98 R, 93 R; 2/DIG. 7

[56] References Cited

U.S. PATENT DOCUMENTS

| | | | |
|---|---|---|---|
| 197,821 | 1/1878 | Briggs | 5/485 |
| 596,842 | 2/1898 | Borwell | 5/484 |
| 1,425,952 | 11/1922 | Fidler | 5/485 |
| 2,351,767 | 6/1944 | Johnson | 5/484 |
| 3,540,441 | 11/1970 | Collins | 128/132 D |
| 3,707,964 | 1/1973 | Patience | 128/132 D |
| 4,097,943 | 7/1978 | O'Connell | 5/484 |
| 4,561,434 | 12/1985 | Taylor | 128/132 R |

Primary Examiner—Stephen C. Pellegrino
Assistant Examiner—J. L. Kruter
Attorney, Agent, or Firm—John M. Cone

[57] ABSTRACT

A sterile, disposable, receiving blanket for a new born baby comprises two bonded layers of sheet material, one of which is relatively absorbent and receives the baby, and the other of which is relatively liquid impervious and acts as a backing sheet. Two sleeves are provided which extend along two opposite edges of the backing sheet on the obverse side from the receiving sheet. Each sleeve is open at one end to receive the hands, wrists and forearms of the nurse or pediatrician using the blanket and is closed at its other end to prevent the hand from contacting the receiving sheet or the baby. The sheets are configured to provide a tapered pouch located in the receiving surface of the blanket and extending across the blanket parallel to and centrally located between the two sleeves. The pouch has a deep end towards the open end of the sleeves which, in use, receives the head of the baby to assist drainage of liquids to the baby's mouth during the initial moments after birth.

8 Claims, 1 Drawing Sheet

RECEIVING BLANKET WITH SIDE SLEEVES

This application is a continuation of application Ser. No. 97,177, filed Sept. 11, 1987 now abandoned.

BACKGROUND OF THE INVENTION

The present invention relates to a novel sterile disposable receiving blanket for use, for example, by a pediatrician or nurse in a delivery room during a routine vaginal birth or a surgically assisted birth.

SUMMARY OF THE INVENTION

In cases of, for example, cesarian birth, the obstetrician attending the mother is gowned, draped and scrubbed to ensure a fully sterile field in the operating area. The delivery field is likewise draped and sterile. After birth, the obstetrician transfers the baby to a pediatrician or another receiving party, such as a nurse, for care. Typically, the pediatrician is not fully scrubbed and gowned so there is less than complete protection against contamination between baby and pediatrician and between the receiving party and the sterile delivery field.

Typically heretofore, the pediatrician receives the baby in a sterilized, reusable, rectangular receiving blanket, which is provided to the pediatrician folded inside a sterile outer wrap. In use, the pediatrician first unwraps and disposes of the outer wrap, then unwraps the blanket, unfolds it and holds it with his fingers at one of its edges, while supporting the blanket at its sides on his arms. Held this way, the blanket presents a surface on which the obstetrician places the baby. During the unfolding and positioning of the blanket on the arms of the pediatrician, the receiving surface of the blanket can be contaminated by the pediatrician's hands, or by contact with a surface in the operating room. In addition, when the baby is received, the pediatrician is at risk of contamination, because his hands and other body parts are undraped and exposed to blood and other material on the baby. There is also a significant risk of contamination of the obstetrician's gown or hands at the time of transfer of the neonate.

It is an object of the present invention to provide an improved receiving blanket for use by a pediatrician or nurse in which the hands and forearms of the receiving party are completely covered when the blanket is in use to prevent contamination of them, or contamination of the receiving surface of the blanket by them, or contamination of the sterile delivery field.

It is a further object to provide an improved receiving blanket which is provided to the operating room folded and sterile and which can be unfolded to receive the baby without touching the baby-receiving surface thereof. It is a yet further object to provide a receiving blanket in which the baby can be securely held by the receiving party and, additionally, in which the drainage of fluids from the baby is assisted by positioning the baby with its head lower than its body.

BRIEF DESCRIPTION OF THE DRAWINGS

The invention will now be described by way of example only, with reference to the accompanying drawings, in which.

DESCRIPTION OF THE PREFERRED EMBODIMENT

Figure 1:
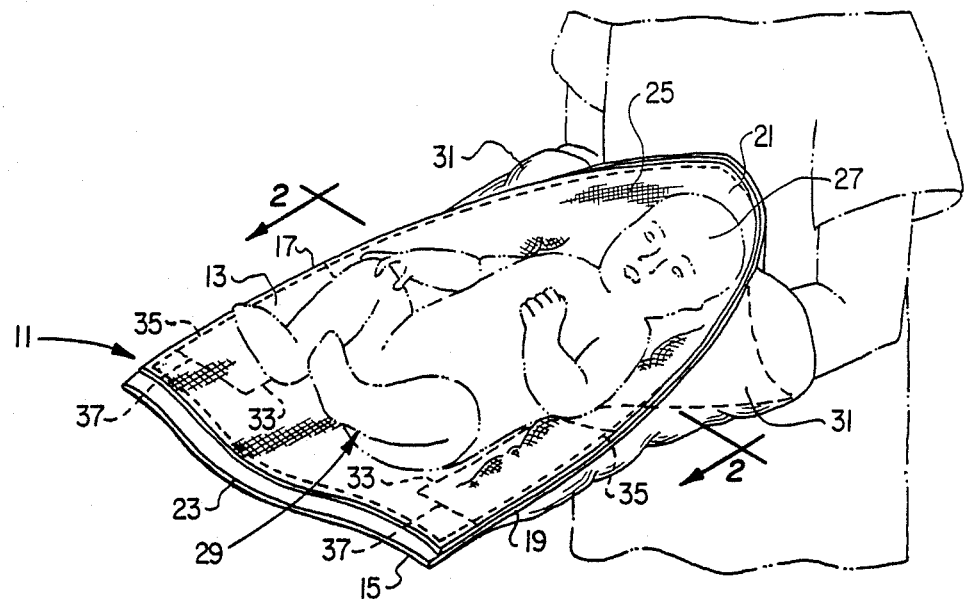
FIG. 1 shows in perspective a sterile disposable receiving blanket embodying the invention, illustrating in phantom the baby received in the blanket and the arms and upper body of the person holding the blanket.

The novel receiving blanket 11 shown in the drawing comprises an inner, baby-receiving surface 13 and an outer, fluid impervious surface 15. The inner surface 13 is, in one form of the invention, a sheet of nonwoven surgical fabric, such as that sold under the registered trademark BARRIER by Surgikos and used, for example for Mayo stand covers. This fabric is relatively absorbent and provides a comfortable surface for the new born baby. The outer surface 15 is formed of a thin, pliable plastic sheet material, such as that used currently for Mayo stand covers, and provides a backing for the inner sheet 13 preventing the transfer of fluids from the baby through the sheet 13 to the pediatrician.

The inner fabric sheet 13 covers substantially all of the inner surface of the outer sheet 15 and is secured thereto either by sewing, as shown in the drawings, or in an alternative form of the invention by an adhesive. Various adhesives have been used commercially to secure, for example, surgical fabric to plastic sheet in Mayo stand covers and the selection of a suitable adhesive is within the knowledge and skill of those with experience in the art.

The sheets 13 and 15 are substantially rectangular having aligned longer sides 17 and 19 and shorter sides 21 and 23 respectively. At one side 21, the longer sides 17 and 19 of the two sheets 13, 15 are gathered together so that a tapered pouch 25 is formed in the receiving surface 13, which extends from the first side 21, at which the pouch 25 has its greatest depth, through the center of the blanket 11 to a point towards the other side 23 at which point it merges into the blanket surface. The pouch 25 extends centrally in the surface 13 midway between the two sides 21 and 23. In use, the pouch 25 receives and supports the head 27 of the baby 29. The exact way in which the pouch 25 is formed and its exact shape may vary within the overall concept of the invention, as will be apparent to those skilled in the art, while still providing support and retention of the baby and positioning of the baby with its head lower than its chest.

On the outer surface of the sheet 15 along each of the major sides 17 and 19 thereof is provided a sleeve 31 which is open at its end adjacent the gathered side 21 and is, advantageously, closed at its other end. The sleeve 31 are located substantially along the respective outer edges 17, 19 of the sheet 15 and are of such length as to enable not only the hands, but also the forearms, of the pediatrician or nurse to be inserted into them, as best seen in FIG. 1.

Figure 2:
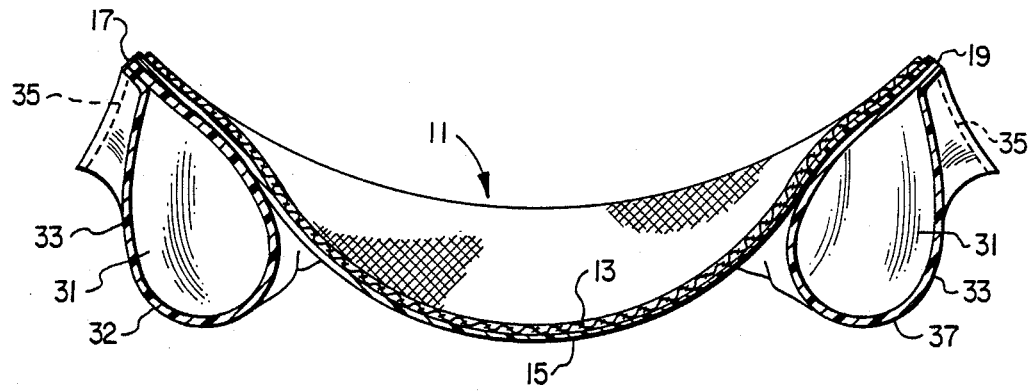
FIG. 2 is a section on the line II—II in FIG. 1.
Figure 3:
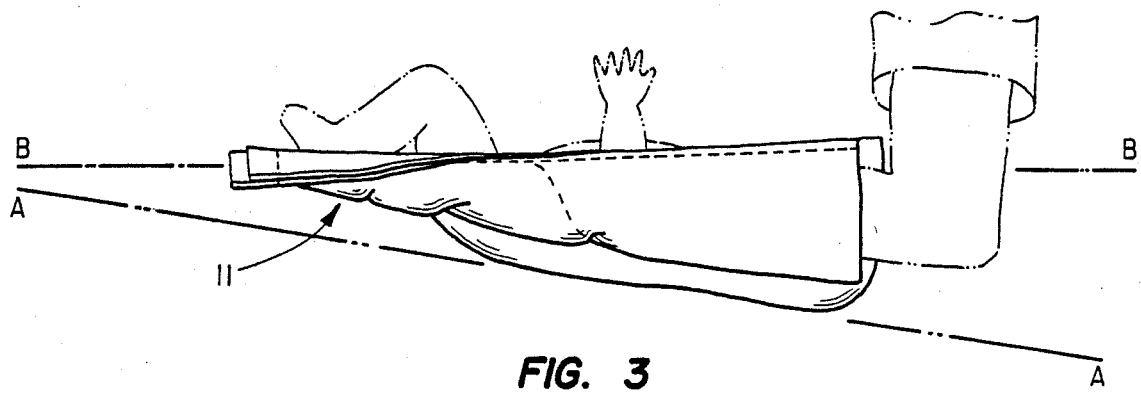
FIG. 3 is a side view of the blanket shown in FIG. 1.

In use, the blanket 11 is provided to the delivery room inside a sterile, disposable outer wrap, not shown. The pediatrician first unwraps the sterile package and then inserts his hands and arms into the sleeves 31. Then he opens and turns the blanket 11 to present to the obstetrician its baby-receiving surface 13 with an essentially flat open end of the surface 13 directed towards the obstetrician and the deep closed, end of the pouch 25 disposed close to the pediatrician. The arms of the pediatrician extend a sufficient distance along the sides of the blanket 11 to fully support the baby when it is placed in the blanket 11, as shown in FIG. 1-3. The pediatrician can now transfer the baby in the blanket to an incubator or other surface, place the blanket and baby on the surface, withdraw his hands and arms from the sleeves 27 and attend to the baby.

In the preferred form of the invention, each sleeve 27 is formed from a substantially cylindrical tube 33 of flexible plastic material, similar to the plastic used for the outer sheet 15, secured, for example, at two spaced apart lines of attachment 33, 35, best seen in FIG. 1, as by sewing, to the underside of the sheet 15 adjacent the edges 17 and 19 thereof. Each sleeve 31 is closed at one of its ends and secured at that end to the sheet 15 as by stitching 37. The sleeves 31 may be formed and attached in ways other than those specifically described, as will be apparent to those skilled in the art.

The outer line of attachment 35 of each sleeve 31 extends substantially the entire length of that sleeve 31. The inner line of attachment 33 is shorter, extending only part of the way from the closed end of the sleeve 31 at attachment line 37 towards the open end of the sleeve 31.

The sleeves 31 are thus able, at their open ends, to separate from the sheet 15, thus allowing the head-receiving pouch 25 of the blanket to hang down between the arms of the user so that, in use, the baby's head is lower than its chest. This is best seen in FIG. 3, in which line A—A represents the line occupied by the neck and head of the baby when it is received in the blanket 11, and line B—B represents the horizontal.

During the transfer of the baby from obstetrician to pediatrician, the blanket 11 provides a barrier between the baby and the pediatrician preventing any contaminating contact, one of the other, and a barrier between the obstetrician and the sterile delivery field.

It will readily be appreciated that blankets embodying the inventive concept described above could also be used to receive contaminated instruments and materials from an operating surface by, for example, a circulating nurse who is not fully gowned and sterile, for safe transfer to a receptacle for disposal.

It will be apparent to those skilled in the art on reading this disclosure that this invention may be practiced in many different ways and has numerous applications beyond the particular receiving blanket described herein. All such practices are considered to be within in the scope of the present invention as defined by the appended claims.

I claim:

1. A receiving blanket for a newly born baby comprising of a substantially rectangular outer sheet of a substantially liquid impervious material having two opposed longitudinal extending peripheral sides; and inner absorbent sheet forming a means to receive the torso of a baby on its outer surface; two open longitudinally extending sleeves secured respectively along each of said opposed peripheral sides, said sleeves forming means of such length to substantially receive and envelope the hands, wrists and a portion of the forearms of a user of said blanket, the portion of the blanket between said sleeves defining a baby receiving portion.

2. A receiving blanket according to claim 1 in which the two sleeves are each open at one end to receive the hands and arms of the user and closed at the other end.

3. A receiving blanket according to claim 1 in which the sleeves are formed of relatively liquid impervious material.

4. A receiving blanket according to claim 1 wherein the relatively liquid impervious material is a flexible plastic sheet material.

5. A receiving blanket according to claim 1 wherein the receiving surface and the outer surface are configured to provide a pouch for receiving, in use, the head of the baby.

6. A receiving blanket according to claim 5 wherein the pouch is of varying depth having a relatively deep end located towards the edge of the blanket between the two open ends of the sleeve and a reducing depth in the direction of the opposite edge to merge into a plane of the blanket.

7. A receiving blanket according to claim 1 wherein the two said surfaces are constituted by two discrete sheets of material which are secured together.

8. A receiving blanket according to claim 1 the two sheets are secured by stitching.

* * * * *